US010695460B2

(12) United States Patent
Schmid et al.

(10) Patent No.: US 10,695,460 B2
(45) Date of Patent: Jun. 30, 2020

(54) COMPOSITION FOR COVERING AND PROTECTING SCARS

(71) Applicant: Siniq GmbH, Wollerau (CH)

(72) Inventors: Juerg Schmid, Wollerau (CH); Andreas Supersaxo, Baar (CH)

(73) Assignee: Siniq GmbH, Wollerau (CH)

( * ) Notice: Subject to any disclaimer, the term of this patent is extended or adjusted under 35 U.S.C. 154(b) by 12 days.

(21) Appl. No.: 15/565,953

(22) PCT Filed: Apr. 14, 2016

(86) PCT No.: PCT/EP2016/058237
§ 371 (c)(1),
(2) Date: Oct. 12, 2017

(87) PCT Pub. No.: WO2016/166220
PCT Pub. Date: Oct. 20, 2016

(65) Prior Publication Data
US 2018/0104379 A1  Apr. 19, 2018

(30) Foreign Application Priority Data

Apr. 16, 2015 (EP) .................................. 15163827

(51) Int. Cl.
*A61L 26/00* (2006.01)
*C08L 33/26* (2006.01)

(52) U.S. Cl.
CPC ....... *A61L 26/0014* (2013.01); *A61L 26/0066* (2013.01); *C08L 33/26* (2013.01); *A61L 2300/802* (2013.01)

(58) Field of Classification Search
None
See application file for complete search history.

(56) References Cited

U.S. PATENT DOCUMENTS

| | | | |
|---|---|---|---|
| 4,699,779 A * | 10/1987 | Palinczar | A61K 8/731 424/59 |
| 5,204,090 A | 4/1993 | Han | |
| 2004/0029969 A1 | 2/2004 | Blatt et al. | |
| 2007/0218021 A1 * | 9/2007 | Wells | A61K 8/062 424/59 |
| 2012/0014882 A1 * | 1/2012 | Singleton | A61K 8/34 424/45 |
| 2014/0148506 A1 | 5/2014 | Thompson et al. | |
| 2014/0170095 A1 | 6/2014 | Halpern et al. | |

FOREIGN PATENT DOCUMENTS

EP  0 055 857 A2  7/1982

OTHER PUBLICATIONS

Lambson Padimate O Technical Data Sheet, Feb. 18, 2015 (Year: 2015).*
Fao.org, Ethyl cellulose, http://www.fao.org/fileadmin/user_upload/jecfa_additives/docs/Monograph1/additive-178-m1.pdf, 1982 (Year: 1982).*
Knowde, Ultra Chemical—CosmoSurf, https://www.knowde.com/companies/ultra-chemical, retrieved online Sep. 4, 2019 (Year: 2019).*
Prospector, CosmoSurf CE-100, https://www.ulprospector.com/en/na/PersonalCare/Detail/5241/332316/CosmoSurf-CE-100, retrieved online on Sep. 4, 2019 (Year: 2019).*
Marshall, L.J., "Muti-talented film formers," COSSMA Apr. 2014, pp. 14-15.
PCT International Search Report for International Application No. PCT/EP2016/058237, dated Jun. 14, 2016.
PCT Written Opinion for International Application No. PCT/EP2016/058237, dated Jun. 14, 2016.
PCT International Preliminary Report on Patentability for International Application No. PCT/EP2016/058237, dated Aug. 1, 2017.
Response to PCT Written Opinion in PCT/EP2016/056237, dated Dec. 22, 2016.
PCT Written Opinion in PCT/EP2016/058237, dated Mar. 22, 2017.
Response to PCT Written Opinion in PCT/EP2016/058237, dated Apr. 27, 2017.
International Preliminary Report on Patentability in PCT/EP2016/058237, dated Jul. 21, 2017.
Information for Arlamol(TM) PS15E, PPG-15 Stearyl Ether, printed from https://www.ulprospector.com/en/na/personalcare/detail/134/97600/Arlamol-ps15e on Sep. 3, 2018.

* cited by examiner

*Primary Examiner* — Jennifer A Berrios
(74) *Attorney, Agent, or Firm* — Sonapat LLC

(57) ABSTRACT

Subject of the invention is a composition comprising: (a) at least one film-forming polymer, which does not comprise silicon, (b) at least one organic UV filter, and (c) at least one organic solvent, wherein the composition is liquid at 20° C., wherein components (a) and (b) are dissolved in solvent (c), and wherein the ratio of the total amounts of organic UV filters (b) to film-forming polymers (a) is below 6.5. The invention also relates to compositions for therapy, uses of the composition, devices and methods.

28 Claims, No Drawings

COMPOSITION FOR COVERING AND PROTECTING SCARS

The invention relates to compositions comprising film-forming polymers, organic UV filters and organic solvent, which are applicable for topical application to scars. The invention also relates to compositions for therapy, uses of the composition, devices and methods.

STATE OF THE ART

A scar is a permanent patch of skin that grows over a wound. Scars are formed of fibrous tissue in a process termed fibrosis. Scarring is a natural part of the wound healing process. With the exception of very minor lesions, every wound, for example resulting from accidents, diseases or surgery, results in some degree of scarring. Scars on the skin can affect the well-being of an individual in various ways. Scars can have an unpleasant optical appearance, especially when formed at exposed sections of the skin. They can also have physiological side effects, such as itching or pain.

In order to relieve such problems, it is common practice to cover scars with pads or patches. Alternatively, they may be covered with protective compositions, such as scar gels. Such covers and compositions provide an improved optical appearance. They also may relieve side effects and promote healing.

Compositions for covering scars and supporting healing of scars are generally provided in the form of silicon-based gels. Silicon gels are capable of occluding the scar from the environment and hydrating the scar. This has a beneficial effect on scar healing, generally referred to as the "occlusion effect".

For example, US 2014/0148506 A1 relates to silicone gels for covering wounds or scars, which are applied to the skin. The gels may comprise common cosmetic or pharmaceutical additives. The gel shall improve scar healing and provide an optically improved appearance to the skin.

Silicon-based scar gels are commercially available, for example under the trademark Dermatix Ultra from MEDA Pharma, Bad Homburg, Del., or under the trademark KELO-COTE from Sinclair Pharma, Frankfurt, Del.

When scars are located at exposed sections of skin, it is important for the user that the scar gel or composition does not impair the individual's activities. It should remain stable on the scar and provide protection for a relatively long time period. It should be transparent and suitable for applying a cosmetic in the color of the skin in order to conceal the scar. Further, occlusion of the scar should be efficient and permanent. In these respects, there is a desire in the art to improve the known compositions.

A composition for regular use, such as a scar gel, should also be applied easily to the skin. The known scar gels based on silica require relatively long drying times of several minutes, which is not convenient for the user.

Further, scars are not pigmented and generally sensitive against UV radiation. Especially UV-A radiation may damage the skin and may have a negative effect on wound healing. Thus, when scars are located at skin portions exposed to the sun, an efficient and long-lasting UV protection is required. However, the capability of silicon-based gels to incorporate common UV filters is generally limited and not sufficient. Thus, the silicon based scar gels, which are presently available, do not provide UV protection or only insufficient UV protection. A silicone based scar gel providing UV protection is commercially available under the trademark KELO-COTE UV from Sinclair Pharma, Frankfurt, Del. However, the level and permanence of UV protection could still be improved.

On the other hand, common sunscreens used in the art can provide high and long-lasting UV protection. Typical sunscreens are described in U.S. Pat. No. 5,204,090 or US 2014/0170095 A1. However, these sunscreens are not adapted to scars. They are typically provided in the form of oils and emulsions. Specifically, they do not cover the skin and seal the skin from the environment. Thus, typical sunscreens do not provide an occlusion effect, which could support scar healing.

Some sunscreens comprise polymer additives, which form polymer films on the skin and stabilize UV filters. When applied to skin, the compositions form oily films, which are thin and transient. Typically, such sunscreens comprise low amounts of film-forming polymers such as about 1% to 2%, and high amounts of UV filters of about 20 to 30%. A commercially available film-forming polymer for use in sunscreen is DERMACRYL 79 (AkzoNobel, US). Ethanol based sunscreen compositions comprising various film-forming polymers in an amount of 1% and 32% UV filters are disclosed in Marshall, L. J., "Multi talented film-formers", COSSMA 4/2014, pages 14/15.

US2004/0029969A1 relates to sunscreens and compositions for treatment of skin damage comprising creatine or derivatives thereof as an active agent. In examples 7 and 8, sunscreen emulsions comprising 0.30 wt. % film forming polymer are disclosed.

EP 0 055 857 relates to topical compositions, such as sunscreen compositions, comprising film-forming polymers. The sunscreen compositions comprise relatively low amounts of UV filters of generally not more than 3% by weight (page 5, lines 13 to 19). The examples show that the UV protection which can be achieved with such compositions is limited. The document does not relate to therapeutical applications or applications for scars.

Thus, there is a need for improved means for covering scars, which provide high and permanent UV protection.

Problem Underlying the Invention

The problem underlying the invention is to provide compositions, uses, methods and devices, which overcome the above mentioned problems. Specifically, the problem is to provide novel compositions for protecting scars, covering scars and supporting healing of scars, which also provide efficient UV protection. The compositions should provide an occlusion effect by sealing and hydrating the scars. The protection should be strong and long-lasting. Specifically, efficient and permanent mechanical protection, UV protection and occlusion should be provided. The everyday outdoor activities of a user should be impaired as little as possible. The composition shall be applied easily and conveniently by the user. The composition shall provide an acceptable optical appearance to the scar. It shall provide a suitable base for cosmetic and therapeutic applications, when appropriate additives are included.

DISCLOSURE OF THE INVENTION

Surprisingly, it was found that the problem underlying the invention is solved by compositions, uses, methods and devices according to the claims. Further embodiments of the invention are outlined throughout the description.

Subject of the invention is a composition comprising
(a) at least one film-forming polymer, which does not comprise silicon,
(b) at least one organic UV filter, and
(c) at least one organic solvent,
wherein the composition is liquid at 20° C., wherein components (a) and (b) are dissolved in solvent (c), and
wherein the ratio of the total amounts in weight percent of organic UV filters (b) to film-forming polymers (a) is below 6.5,
wherein the overall amount of UV filters (b) in the composition is at least 10% w/w).

Subject of the invention is also the composition for use in therapy.

Preferably, the therapy is for supporting healing of a scar. Preferably, the composition is applied locally and topically to a scar of an individual. The scar could be of any type, such as a keloid, hypertrophic scar, atrophic scar or stretch mark.

Subject of the invention is also a non-therapeutic use of the composition for locally covering and/or protecting a scar, especially providing UV protection to a scar.

The composition is a liquid solution. Thus, components (a) and (b) and any additives are dissolved in the solvent. Thus, the composition does not comprise two phases or solids dispersed therein. It is not an emulsion or suspension, for example in the form of a lotion, cream or gel.

The ratio of the total amounts of organic UV filters (b) to film-forming polymers (a) is below 6.5. In other words, the content of polymers in the composition is relatively high. Such a high level of film-forming polymers (a) is not normally used in sunscreen compositions. When the composition is applied to skin, a coating having a novel structure and properties is formed. According to the invention, a solid, elastic coating is formed due to the high polymer content, whereas compositions of the art comprise lower amounts of polymers and form oily films upon application to skin.

As used herein, the term "film-forming polymer" refers to a polymer in the composition, which forms a uniform coating when the composition is applied to skin in a thin layer and the organic solvent is evaporated. Typically, such polymer films are formed uniformly and continuously on the skin. In contrast, other non-film-forming polymers form discrete structures and agglomerate in "islands". Preferably, the polymer is not cured. Thus, the polymer preferably does not form a covalently linked network during or after coating formation. The coating binds the UV filter on the skin. Film-forming polymers for use in cosmetic compositions, such as sunscreens, are known and widely used in the art. Typical organic UV filters support formation of a uniform coating, because they function as plasticizers in the polymer mixture. Specifically, the film-forming polymer forms a film on skin when applied in a typical sunscreen solution with organic UV filters and organic solvent, especially ethanol.

The film-forming polymer is compatible with the organic solvent, especially alcohols, and can be dissolved easily. In a specific embodiment, the film-forming polymer is not water-soluble.

The film-forming polymer does not comprise the element silicon (Si). Thus, the film-forming polymer is not a silicone. The at least one film-forming polymer it is carbon-based. Preferably, it consists of elements C, H, O and N, optionally also S. Depending on the structure, the polymer may comprise counter-cations, such as alkaline metal or alkaline earth metal ions or ammonium. Preferably, the composition does not comprise a film-forming polymer, which comprises silicon, at all. In a specific embodiment, the composition does not comprise a silicone or a compound comprising silicon (Si) at all.

In a preferred embodiment, the film-forming polymer is a copolymer. As used herein, the term "copolymer" refers to any polymer prepared from 2 or more monomeric subunits. Thus, the term copolymer encompasses terpolymers, tetrapolymers and the like. It may be of any known structure, such as an alternating, periodic, statistical or block copolymer.

Preferably, the copolymer is amphiphilic. In other words, it comprises hydrophilic and hydrophobic groups. Without being bound to theory, it is believed that amphiphilic polymers conveys advantageous properties to the compositions, because the hydrophobic groups may form a water barrier and seal the scar, whereas the hydrophilic groups may have positive impact on the scar surface and water balance. Preferably, the hydrophilic groups are attached to the polymer main chain and the hydrophobic groups form side chains.

Preferably, the hydrophilic groups are carboxyl groups. Without being bound to theory, carboxyl groups may have a positive impact on the water balance of the scar. Preferably, the carboxyl groups are repetitive subunits, which are preferably attached directly to the main chain of the polymer.

Preferably, the hydrophobic groups are alkyl groups. Without being bound to theory, alkyl groups may participate in binding and stabilization of the organic UV filters in the film as well as providing good water repellent properties. The alkyl groups may comprise 2 to 30, preferably 2 to 20, more preferably 6 to 12 carbon atoms. The alkyl groups could be branched or linear. Preferably, the alkyl groups are repetitive subunits. More preferably, they form side chains of the polymer. Such side chains are linked to the polymer main chain. They are not part of the polymer main chain and do not link monomeric subunits with each other. Without being bound to theory, the length of the alkyl side chain seems to control water repellent properties of the coating. Thus, in a preferred embodiment, the alkyl side chain comprises at least 4 or at least 6 carbon atoms.

In a preferred embodiment, the copolymer comprises carboxyl groups and alkyl groups. The carboxyl groups are attached to the polymer main chain and the alkyl groups are side chains. The side chains are attached laterally to the main chain.

In a preferred embodiment, the film-forming-polymer is an acrylate. Acrylates comprise carboxyl groups attached to the main chain of the polymer. Preferably, the film-forming polymer (a) is an acrylate/amide copolymer. Preferably, the polymer is an acrylic copolymer with hydrophobic groups, more preferably an acrylate/amide copolymer with hydrophobic groups. Most preferably, the polymer is an acrylate/amide copolymer with alkyl groups having 6 to 16 carbon atoms. In a highly preferred embodiment, the polymer is acrylates/octylacrylamide copolymer (INCI name; CAS Nr. 129702-02-9). This polymer is commercially available, for example under the trademark DERMACRYL 2.0 or DERMACRYL 79 from AkzoNobel, Del. Such polymers comprise carboxyl groups attached to the polymer main chain and octyl side chains.

In another embodiment, the film-forming polymer is a polyester. The polyester may comprises carboxyl groups and alkyl side chains. Preferably, the copolyester is prepared from maleic acid, more preferably it is (partial) ethyl ester of copolymer of methyl vinyl ether/maleic acid (CAS number 25087-06-3). Such polymers are commercially available under the trademark Gantrez SP 215 from Ashland, US.

However, if the alkyl side chain length is short, the water repellent properties may not be optimal.

Another applicable film-forming polymer hydrogenated dimer dilinoleyl/dimethylcarbonate copolymer, available from BASF, DE, under the trademark COSMEDIA DC. However, the polymer is not preferred because the coating prepared on the skin tends to be tacky. Other film-forming polymers are copolymer of vinylpyrrolidone and a long-chain alpha-olefin, commercially available under the trademark GANEX V220 from Ashland, US; vinylpyrrolidone/tricontanyl copolymers available as GANEX WP660 from Ashland, US; water-dispersible polyesters, including sulfopolyesters, available from Eastman Chemical under the trademark EASTMAN AQ 38S.

Preferably, the amount of the film-forming polymer (a) in the composition is above 4%, preferably above 5% (w/w), more preferably above 6% or above 7%. Preferably, the amount is from above 5% to 50% (w/w), more preferably from 6% to 30% (w/w) or from 7% to 25%. In a specific embodiment, the amount is from 8% to 25% (w/w) or from 8 to 20% (w/w). Such high amounts of film-forming polymers are unusual in sunscreens of the prior art. Typical sunscreens comprise lower amounts of film-forming polymers from about 1 to 2% (w/w). Unless explicitly stated otherwise, all amounts throughout this application are provided in weight percent (% w/w).

The composition comprises at least one organic UV filter (b). Organic UV filters for use in sunscreen compositions are known in the art. In principle, any organic UV filter is applicable, which is compatible with and preferably soluble in the organic solvent.

Preferably, more than one UV filter is used, for example 2, 3, 4, 5, 6 or more UV filters. Preferably, the composition comprises 2 to 10, or 3 to 6 UV filters. Typically, sunscreen compositions comprise combinations of UV filters, because multiple UV filters provide better protection over a broad range of the UV spectrum. UV filters or combinations of UV filters for use in the composition are selected in view of the desired UV protection. Generally, a combination of two, three or more UV filters is advantageous for protection over a broad wavelength range.

Preferably, the organic UV filter absorbs radiation in at least a portion of the ultraviolet spectrum (290 nm-400 nm) and/or has at least one absorption peak in this spectrum. Preferably, the organic UV filter has a specific extinction (1%, 1 cm,) in ethanol of more than 50, preferably more than 100 or more than 200, for at least one wavelength in the ultraviolet spectrum.

Organic UV-filters, that are useful in the present invention, are cosmetically acceptable. Preferably, the UV filter is listed in the International Nomenclature of Cosmetic Ingredients (INCI). Preferably, the UV filter is approved for use by the European Community or FDA (USA).

Typically, the organic UV filter is an aromatic compound, which is conjugated with at least one carbonyl group, ester group and/or amide group. Typical organic UV filters for use in the inventive composition are amiloxate, 4-aminobenzoic acid, avobenzone, bemotrizinol, benzophenone-n, bisdisulizole disodium, bisoctrizole, cinoxate, dibenzylid, eneacetone, diethylamino hydroxybenzoyl hexyl benzoate, dioxybenzone, drometrizole trisiloxane, ecamsule, ethylhexyl triazone, homosalate, iscotrizinol, menthyl anthranilate (meradimate), 4-methylbenzylidene camphor (enzacamene), mexenone, octocrylene, octyl methoxycinnamate, ethylhexyl methoxycinnamate (octinoxate), octyl salicylate (octisalate), oxybenzone, padimate A, padimate O, phenylbenzimidazole sulfonic acid (ensulizone), sulisobenzone, trolamine salicylate, and umbelliferone. Preferably, the composition comprises at least one UV filter, preferably at least 2 or at least 3 from this list of UV filters.

Further specific examples of organic UV-filters (in brackets: trademark, manufacturer), that may be used in compositions of the present invention include, octocrylene (Parsol 340, DSM), isoamyl-p-methoxycinnamate (Neo Heliopan E1000, Symrise), butyl methoxydibenzoylmethane (Parsol 1789, DSM), diethylamino hydroxybenzoyl hexyl benzoate (Uvinul A Plus, BASF), benzophenone-3 (i.e., oxybenzone), 2-Hydroxy-4-methoxyphenyl)-(2-hydroxyphenyl)methanone (i.e., dioxybenzone), 2-(2H-benzotriazol-2-yl)-4-methylphenol, also known as drometrizole trisiloxane (also known as MEXORYL XL), butylmethoxy dibenzoylmethane ("avobenzone"), 4-methyl benzilidene camphor ("4-MBC"), ethylhexyl triazone (available as UVINUL T-150 from BASF, DE), bemotrizinol (available as TINOSORB S from BASF), menthyl-2-aminobenzoate ("menthyl anthranilate"), 4-aminobenzoic acid ("PABA") and hydroxy methylphenyl benzotriazole.

In a specific embodiment of the invention, the organic UV filter (b) is selected from octocrylene, isoamyl-p-methoxycinnamate, butyl methoxydibenzoylmethane and diethylamino hydroxybenzoyl hexyl benzoate.

The composition does not comprise inorganic UV filters, such as zinc or titanium oxide. The UV filter may be an organic compound, which also comprises Si.

The overall amount of UV filters (b) in the composition is at least 10% (w/w). Preferably, the amount is at least 15% or at least 20% (w/w). Preferably, the amount is between 10% and 60%, preferably between 15% and 50%, more preferably between 20% and 40% (w/w).

The composition comprises at least one organic solvent (c), in which the film-forming polymer (a) and organic UV filter (b) are soluble. The solvent should be volatile at room temperature, such that it evaporates rapidly after administration to the skin. Preferably, the solvent is selected from an alcohol, ethyl acetate, acetone and methylal. Preferably, the alcohol is a monohydroxyl alcohol. Preferably, the alcohol is an aliphatic alcohol comprising one to five carbon atoms. Preferably, the alcohol is selected from ethanol, propanol or isopropanol. Most preferably, the alcohol is ethanol. In principle, the alcohol is selected to be compatible with relatively high amounts of polymers (a) and UV filters (b) to be cosmetically acceptable, and to evaporate rapidly such that a coating is formed soon after topical application of the composition.

The amount of organic solvent in the composition may be from 30% to 90% (w/w), preferably from 40% and 80% (w/w), more preferably between 50% and 70% (w/w). Preferably, the composition comprises less than 5% (w/w) water, preferably less than 2% (w/w) or less than 1% (w/w). Preferably, the composition is essentially water-free. Preferably, no water is added to the composition, especially during production and use. The low amount or absence of water or water is advantageous, because the organic solvent can evaporated more rapidly. Further, it was found that the overall composition is highly stable in ethanol.

Next to components (a) to (c), the composition may comprise additives (d). Additives for cosmetic compositions, sunscreen compositions and scar gels are known in the art. The additives are selected and applied in amounts such that the overall composition is liquid.

In a preferred embodiment of the invention, the composition further comprises at least one additive (d) selected from moisturizers, photoprotective agents, hydrophobic ingredients, such as oils, fats and waxes, surfactants, thickening agents, fragrances, dyes, preservatives, photostabilizers, antioxidants, skin care agents or pharmaceutical compounds. The additives are dissolved in the composition.

In a preferred embodiment, the composition comprises a photoprotective agent. Photoprotective agents prevent or reduce damages from radiation on a physiological or pharmacological level. Preferably, the photoprotective agent is equal.

In a preferred embodiment, the composition comprises an antioxidant, such as tocopherol (vitamin E). Preferably, the composition comprises a moisturizer, preferably selected from lecithin, vitamin E, glycerine or dexpanthenol. In a preferred embodiment, the composition comprises at least one hydrophobic compound, such as oil, such as a mono-, di- or triglyceride, fats, waxes or the like.

In a specific embodiment, the composition does not comprise other polymers than the film-forming polymers (a). Preferably, the composition does not comprise silicon-based polymers, especially silicone polymers. Surprisingly, it was found that the composition efficiently protects scars even without silicones, whilst a high UV protection is achieved.

In a preferred embodiment of the invention, the composition consists of
 (a) between 5 and 50%, preferably 6 to 30% (w/w) film-forming polymers, which do not comprise silicon,
 (b) between 10 and 60%, preferably 15 to 50% (w/w) organic UV filters,
 (c) between 30 and 90%, preferably 40 to 80% (w/w) organic solvents, and
 (d) between 0 to 25%, preferably between 0 to 10% (w/w) additives.

The amounts of polymer (a), UV filters (b), solvents (c) and additives (d) are adjusted to each other such that a solid coating is formed after application to a scar surface. In principle, polymers and UV filters are used in amounts such that the overall composition is homogenous and has sufficient viscosity to be administered uniformly to the skin. A relatively low concentration of solvent is advantageous for achieving rapid evaporation and coating formation. It goes without saying that the concentrations of components (a), (b) and (d) are limited by their solubility in the solvent and compatibility with the other components. In this respect, it is advantageous that typical organic UV filters can be mixed with typical film-forming polymers, and that both are highly compatible with typical organic solvents for cosmetic and pharmaceutic applications, such as ethanol.

The composition is a liquid solution. Thus, it can be applied easily to the skin as a thin, uniform layer. After application to the skin, the solvent evaporates rapidly. After solvent evaporation, a coating remains on the skin.

In the composition, the ratio of the total amounts (w/w) of organic UV filters (b) to film-forming polymers (a) is below 6.5. Preferably, the ratio is below 6 or below 5.5. More preferably, it is below 5 or below 4, in certain applications also below 3. Preferably, the ratio is at least or above 1, preferably at least 1.5 or at least or above 2. Preferably, the ratio is between or above 1 and 6.5, more preferably between 1.5 and 5.5 or between or above 2 and 4. In a highly preferred embodiment, the ratio is above 1 or above 2. The ratios used herein are calculated by dividing the total amount (w/w) of all organic filters (b) in the composition by the total of all film-forming polymers (a) in the composition. When the ratio is above 6.5, the amount of polymer is usually not sufficient for forming a solid coating. If too little polymer is used, the coating tends to become an oily film. When the ratio is 1 or less, the amount of UV filters becomes relatively low and it is more difficult to provide efficient UV protection in a thin coating.

Common sunscreens comprise low levels of film-forming polymers of about 1 to 3% and high amounts of organic UV filters of about 20 to 30%. Typically, the ratio of film-forming polymers (a) to UV filters (b) in such sunscreen compositions is from about 8 to about 20, often around 10. When applying such compositions to skin, oily films are formed.

In a highly preferred embodiment, the composition comprises at least 5% (w/w) of film-forming polymers (a), the ratio of the total amounts in weight percent of organic UV filters (b) to film-forming polymers (a) is above 1, more preferably above 2, and the composition has a sun protection factor (SPF) of at least 10, more preferably at least 20.

In the inventive composition, the ratio of polymer to UV filters is significantly lower than in known compositions. As a result, a thin solid coating is formed when the inventive composition is applied to skin. The properties of such a solid coating are strikingly different from those of an oily film. The inventive coating is elastic, has high abrasion resistance, adheres to the skin and is essentially water resistant. Sunscreens used in the art do not form such solid coatings. The ratio of polymer to UV filters is adjusted higher, because a solid coating would not be acceptable for common sunscreen applications, for example due to the physical properties and lack of moisture permeability. It was also observed that the inventive solid coating is not obtainable when applying several layers or a thick layer of common sunscreen to skin.

The coating is highly advantageous for local and topical covering of scars. The coating seals the scar and prevents water exchange with the environment, thereby providing an occlusion effect which supports scar healing. The coating is stable and shields the scar from the environment. The coating provides efficient UV protection, but also mechanical protection. Both is highly important for scar tissue in the process of healing and for the new skin formed, which lacks strength and pigments. Further, it was found that such a coating is permanent and provides long term protection.

Without being bound to theory, the UV filters seem to be embedded at least in part in the coating. The coating provides efficient UV protection. Further, the coating provides UV protection for a relatively long time. Preferably, the UV protection of the coating is provided for a period of 4, 8, 12 or 24 hours. In this respect, this could mean that the SPF is not reduced by more than 10%, more than 20% or more than 50% during such a time period.

In a preferred embodiment, the composition has a sun protection factor (SPF) of at least 10, at least 20, preferably at least 30, at least 40 or at least 50. Preferably, this SPF is against UV-A and/or UV-B, more preferably against UV-A and UV-B. As used herein, the UV range and subranges are defined as in DIN 5031-7 (UV-A: 380-315 nm; UV-B: 315-280 nm). In a highly preferred embodiment, the SPF is above 30. Preferably, the SPF is determined according to EN ISO 24444:2010. In this standard method, a composition is administered such that 2 mg/cm$^2$ remain after solvent evaporation. The UVA Protection is determined according to ISO 24443:2012 (in vitro method). Preferably, the critical wavelength $\lambda_c$ is at least 370 nm, determined according to the COLIPA method for in vitro UVA-determination.

The composition is applied as a thin layer. The amount of composition is adjusted such that the site of application is completely covered by the coating and that the coating is continuous. Preferably, the amount of liquid composition administered is between 1 and 10 mg/cm² and/or the amount of dry coating is between 0.5 and 5 mg/cm².

The coating is essentially water resistant. This means, that a water drop on the coating remains on the surface, and does not enter or pass the coating. This is advantageous if the user is in contact with water, for example during rain, swimming or bathing.

The water vapor permeability of the coating is relatively low. Thus, water cannot pass the coating and the occlusion effect is enhanced. Typical sunscreen known in the art may be water repellant to a certain degree and temporarily. However, their water vapor permeability is typically higher than that of the inventive compositions.

The coating adheres firmly to the skin. It has a high stability against mechanical disruption, especially abrasion. This is highly advantageous for everyday use, for example if the user wears clothing above the scar.

Preferably, the coating has a low tackiness. This means that the coating is not tacky on the front side, which is opposite to the skin. In contrast, the back side of the coating has good adherence to the skin. Low tack can be achieved if the film-forming polymer is selected appropriately. As outlined above, it was found that amphiphilic film-forming polymers may confer low tack to the coating. In contrast, it was found that tacky coatings can be obtained with other film-forming polymers, such as hydrogenated dimer dilinoleyl/dimethyl carbonate copolymer.

The coating has a high stability after application to the skin and drying. It was found that the coating tightly seals the skin and provides UV protection even for long time spans, such as 4 or 8 hours. For example, the UV protection (SPF) provided 8 hours after application could still be at least 50% of the initial level.

The viscosity of the liquid composition may be between 10 and 1000 mPas, preferably between 15 and 500 mPas, more preferably between 20 and 200 mPas (determined at 20° C. according to DIN 53015, ISO 12058).

Preferably, the composition is a clear solution. Thus, the coating is transparent or clear. This is advantageous, because the coating is discreet and not eye-catching. If desired, it may comprise a colorant in skin colour, or could be coloured after drying.

The composition can be administered to as scar in a method for covering a scar, comprising the steps of
(A) providing the composition, and
(B) applying the composition locally and topically to a scar of an individual.

The method may be a non-therapeutic method. Preferably, the method is for providing UV protection to the scar. In step (B), the composition should be applied uniformly.

Preferably, the method comprises a subsequent step of
(C) drying the composition.

The composition dries rapidly after application to the skin. Preferably, the composition dries in less than 60 seconds, more preferably in less than 40 seconds, even more preferably in less than 30 seconds, typically in about 20 to 30 seconds. No drying means are required. Such a rapid self-drying is possible because the coating is thin and the amount of composition required for a stable and tight coating is low. Further, drying is supported by the temperature of the human skin and the large surface. The short drying time is advantageous for the user for regular and frequent use and renders the composition acceptable.

Subject of the invention is also a device for topical application of the composition to the skin of an individual, wherein the device comprises the composition. The composition can be applied to the skin by known means. It may be stored in and delivered from the device. In principle, any device is applicable which delivers a thin layer on the skin. Preferably, the device is a roller, flow pen, spray container or bottle. It was found that a highly uniform, continuous and thin coating can be obtained with a roller. Preferably, the roller could be a single-ball roller or a tri-ball roller. The flow pen could be a flow pen with a silicone tip or flap. In other embodiments, the composition is applied from a bottle, for example with a brush, dosing pipet, spatula, cloth, stick, cotton pad or the like.

In a preferred embodiment, the composition is cooled before application, for example to a temperature between −10° C. and +10° C. Preferably, the composition is applied with a cooled roller.

Subject of the invention is also a method for producing the inventive composition, comprising the steps of
(i) dissolving the film-forming polymers (a) in alcohols (c) to obtain phase A,
(ii) providing the UV filters (c) in liquid form, optionally at enhanced temperature, as phase B, and
(iii) mixing phase A and phase B, preferably by adding phase B to phase A.

Preferably, steps (i), (ii) and/or (iii) are carried out with mixing means, preferably under stirring. Preferably, phase A is maintained at room temperature. If the UV filters (c) are solid or not sufficiently vicious at room temperature, they are preferably heated in step (ii) in order to obtain a liquid phase B. Subsequently, the phases A and B are mixed. Preferably, in step (iii) phase B is slowly added to phase A under mixing, preferably stirring. All the steps are carried out such that a homogeneous, clear solution is obtained in step (iii).

The inventive composition and use are preferably for local application of the composition to a scar. This means that the composition is applied specifically to the scar, possibly also to a relatively small area of skin which surrounds the scar. Covering an area which surrounds the scar may be advantageous for improving adherence or occlusion. Normally, the inventive composition is not distributed widely on the skin such as common sunscreens.

The composition or use could be non-therapeutic, especially cosmetic, or therapeutic. Specifically, the therapeutic composition is for supporting or improving healing of a scar. The therapeutic composition may actively promote healing of the scar or ease side effects of the scar, such as itching or pain. Preferably, the therapeutic effect is mediated by sealing the scar with the coating. Then, the coating hydrates the scar and provides an occlusion effect, which supports healing. A therapeutic composition may also prevent the scar from damage on a molecular level. This may be achieved by including active ingredients having a therapeutic effect, such as photoprotective agents, especially equal.

The composition could be for a non-therapeutic use, such as a cosmetic use. For example, the composition could be used basically as a sunshield. Typically, the non-therapeutic use is not basically mediated by ingredients, which actively support healing of the scar on a physiological or molecular level. A cosmetic use can also be for improving the optical appearance of the scar.

The inventive composition, method, use and device solve the problem underlying the invention. A composition is provided, which supports scar healing. It provides occlusion of a scar combined with efficient UV protection. The water vapour permeability is low. Occlusion is associated with hydration and beneficial effects on scar healing. Application of the composition is easy and regular use is convenient. Specifically, the composition can easily be applied to the skin with a roller or the like and dries rapidly, typically within less than 60 seconds. The coating is water resistant and adheres firmly to the skin. The coating provides long-lasting protection against UV and against disruption, for example due to abrasion. Thus, typical activities of the user, in which skin is exposed to UV, are not impaired. Due to the mechanical stability against abrasion, the cover is not affected if clothing is worn or changed on top of the coating. The transparent coating is optically discreet and can be modified with make-up, if desired. The components of the composition are cosmetically and pharmaceutically acceptable and easily available. The method for preparing the composition is simple.

EXAMPLES

Example 1

TABLE 1

Composition example 1

| Pos. | INCI Name (trade name, manufacturer) | CAS Number | Dosage [%, w/w] | Function |
|---|---|---|---|---|
| 1 | alcohol (--, Alcosuisse) | 64-17-5 | 55.0 | solvent |
| 2 | acrylates/octylacrylamide copolymer (Dermacryl 2.0, AkzoNobel) | 129702-02-9 | 15.0 | film-forming polymer |
| 3 | octocrylene (Parsol 340, DSM) | 6197-30-4 | 10.0 | UV filter |
| 4 | isoamyl-p-methoxycinnamate (Neo Heliopan E1000, Symrise) | 71617-10-2 | 10.0 | UV filter |
| 5 | diethylamino hydroxybenzoyl hexyl benzoate (Uvinul A Plus, BASF) | 302776-68-7 | 10.0 | UV filter |

Preparation

Phase A

Add the solvent (Pos. 1) into a receiving vessel.

Add the polymer (Pos. 2) to the solvent (Pos 1) and start to stir. Continue to stir at ambient temperature until a clear and homogenous liquid is obtained.

Phase B

Add the UV filters (Pos. 3, Pos. 4 and Pos. 5) into a separate vessel and start to stir.

Heat up to max. 65° C. and continue to stir until a clear and homogenous liquid is obtained.

Composition

Add phase B to phase A and mix by stirring at room temperature until a clear, slightly viscous and homogenous liquid is obtained, which had a viscosity (20° C.) of 98 mPas and a density (20° C.) of 0.912 g/cm$^2$.

Administration and Product Properties

Using a roll-on, a brush or another suitable applicator the slightly viscous Polymer-UV filter solution can be easily administered onto a scar. Shortly after application the solvent evaporates and a thin coating is formed. The coating is solid and elastic. It is water-resistant, non-tacky and hard to rub off. The formed coating is occlusive and protects the scar from UV radiation.

Example 2

TABLE 2

Composition example 2

| Pos. | INCI Name (trade name, manufacturer) | CAS Number | Dosage [%, w/w] | Function |
|---|---|---|---|---|
| 1 | alcohol (--, Alcosuisse) | 64-17-5 | 60.0 | solvent |
| 2 | acrylates/octylacrylamide copolymer (Dermacryl 2.0, AkzoNobel) | 129702-02-9 | 15.0 | film-forming polymer |
| 3 | octocrylene (Parsol 340, DSM) | 6197-30-4 | 10.0 | UV filter |
| 4 | isoamyl-p-methoxycinnamate (Neo Heliopan E1000, Symrise) | 71617-10-2 | 10.0 | UV filter |
| 6 | butyl methoxydibenzoyl-methane (Parsol 1789, DSM) | 70356-09-1 | 5.0 | UV filter |

The preparation was carried out in a way that is analogous to example 1. The properties of the coating were essentially as described in example 1.

Example 3

TABLE 3

Composition example 3

| Pos. | INCI Name (trade name, manufacturer) | CAS Number | Dosage [%, w/w] | Function |
|---|---|---|---|---|
| 1 | alcohol (—, Alcosuisse) | 64-17-5 | 61.0 | solvent |
| 2 | acrylates/octylacrylamide copolymer (Dermacryl 2.0, AkzoNobel) | 129702-02-9 | 15.0 | film-forming polymer |
| 3 | octocrylene (Parsol 340, DSM) | 6197-30-4 | 8.0 | UV filter |
| 4 | isoamyl-p-methoxycinnamate (Neo Heliopan E1000, Symrise) | 71617-10-2 | 8.0 | UV filter |
| 5 | diethylamino hydroxybenzoyl hexyl benzoate (Uvinul A Plus, BASF) | 302776-68-7 | 8.0 | UV filter |

The preparation was carried out in a way that is analogous to example 1. The properties of the coating were essentially as described in example 1.

Example 4

TABLE 4

Composition example 4

| Pos. | INCI Name (trade name, manufacturer) | CAS Number | Dosage [%, w/w] | Function |
|---|---|---|---|---|
| 1 | alcohol (--, Alcosuisse) | 64-17-5 | 66.0 | solvent |
| 2 | acrylates/octylacrylamide copolymer (Dermacryl 2.0, AkzoNobel) | 129702-02-9 | 15.0 | film-forming polymer |
| 3 | octocrylene (Parsol 340, DSM) | 6197-30-4 | 7.0 | UV filter |
| 4 | isoamyl-p-methoxycinnamate (Neo Heliopan E1000, Symrise) | 71617-10-2 | 7.0 | UV filter |
| 6 | butyl methoxydibenzoyl-methane (Parsol 1789, DSM) | 70356-09-1 | 5.0 | UV filter |

The preparation was carried out in a way that is analogous to example 1. The properties of the coating were essentially as described in example 1.

Example 5

TABLE 5

Composition example 5

| Pos. | INCI Name (trade name, manufacturer) | CAS Number | Dosage [%, w/w] | Function |
|---|---|---|---|---|
| 1 | alcohol (—, Alcosuisse) | 64-17-5 | 57.6 | solvent |
| 2 | ethyl ester of PVM/MA copolymer (Gantrez SP 215, Ashland) | 25087-06-3 | 20.0 | film-forming polymer |
| 3 | octocrylene (Parsol 340, DSM) | 6197-30-4 | 10.0 | UV filter |
| 4 | isoamyl-p-methoxycinnamate Neo Heliopan E1000, Symrise) | 71617-10-2 | 7.4 | UV filter |
| 6 | butyl methoxydibenzoylmethane (Parsol 1789, DSM) | 70356-09-1 | 5.0 | UV filter |

The preparation was carried out in a way that is analogous to example 1. The properties of the coating were essentially as described in example 1, but the water resistance of the coating was not as good as the one of example 1.

Example 6

A composition was prepared essentially according to example 1, but the film-forming polymer was hydrogenated dimer dilinoleyl/dimethylcarbonate copolymer (BASF, DE, trademark COSMEDIA DC) instead of Dermacryl 2.0. The properties of the coating were essentially as described in example 1, but the coating was found to be tacky.

Examples 7 to 11

The influence of the ratio of UV-filters to film-forming polymers on the coating characteristics was studied in a series of experiments. The properties of various alcoholic solutions containing equal amounts UV-filters but different amounts of the polymer Dermacryl 2.0 were assessed. The formulations of examples 7 to 11 were prepared as described in example 1, but the amount of polymer was changed. The amount of ethanol was adapted to the change of polymer. Examples 7 to 10 are inventive and example 11 is comparative. The changes compared to example 1 and the results obtained are summarized in the following table.

TABLE 6

Compositions of examples 1 and 7 to 11

| Ex. | Dermacryl 2.0 [wt. %] | Ethanol [wt. %] | Ratio* | Film Characteristics |
|---|---|---|---|---|
| 1 | 15.0 | 55 | 2.0 | clear<br>firm and elastic feel<br>tack-free adhesion<br>excellent skin substantivity and persistency<br>water and rub-off resistant<br>suitable for applying cosmetics to conceal the scar |
| 7 | 12.5 | 57.5 | 2.4 | as ex. 1 |
| 8** | 10.0 | 60 | 3.0 | as ex. 1 |
| 9 | 7.5 | 62.5 | 4.0 | as ex. 1 |

TABLE 6-continued

Compositions of examples 1 and 7 to 11

| Ex. | Dermacryl 2.0 [wt. %] | Ethanol [wt. %] | Ratio* | Film Characteristics |
|---|---|---|---|---|
| 10 | 5.0 | 65 | 6.0 | clear<br>slightly oily<br>slightly tacky<br>good skin substantivity and persistency<br>water resistant<br>partially removable<br>limited suitability for permanently applying cosmetics to conceal the scar |
| 11 | 4.5 | 65.5 | 6.7 | oily and greasy feel<br>easy to remove<br>not suitable for permanently applying cosmetics to conceal the scar |

*total UV-filters to polymer weight ratio
**viscosity determined to be about 36 mPas The results show that alcoholic solutions, which are containing equal amounts of UV-filters but varying amounts of the polymer Dermacryl 2.0, exhibit different coating forming properties. Formulations containing 7.5% or more of the polymer form clear, firm, elastic and tack-free coatings exhibiting good skin substantivity and persistency. The coatings are water and rub-off resistant. In contrast, the solution containing only 4.5% of the polymer forms a clear film with an oily feel. The coating can be easily removed. From the data, it can be deduced that a UV-filter to polymer ratio of less than 6.7, preferably less than 6, is required for obtaining coatings with the desired characteristics for scar treatment: clear, firm, elastic, tack-free, occlusive, good skin substantivity, water and rub-off resistant. This ratio might be slightly different depending on the UV-filter combination used and should be evaluated for each set of UV-filters.

Examples 12 to 19—UV Protection, Application and Stability of Coating

The UV protection properties, application and mechanical stability of an inventive coating of a composition according to example 8 above were analyzed. For comparison, the same methods were carried out under identical conditions with a commercial scar protection product available under the trademark KELO-COTE UV from Sinclair Pharma, DE. This silicone based scar gel is the market leader for scar and UV protection and thus a suitable benchmark product for direct comparison.

Examples 12 to 15—Mean Sun Protection Factor SPF

The mean sun protection factor (SPF) was determined according to DIN EN ISO 24444:2010, a method for the in vivo determination of the sun protection factor of sunscreen products. It is applicable to products that contain any component able to absorb, reflect or scatter UV rays and which are intended to be placed in contact with human skin. This international standard provides a basis for the evaluation of sunscreen products for the protection of human skin against sunburn induced by solar ultraviolet rays. The level of sun protection provided by sunscreen products has traditionally been estimated using the sun protection factor or SPF test, which uses the erythemal response of the skin to UV radiation. The SPF is a ratio calculated from the energies required to induce a minimum erythemal response with and without sunscreen product applied to the skin of human volunteers. It uses ultraviolet radiation usually from an artificial source. The test was carried out with 10 individuals. Results were determined 30 min and 8 h after application to the skin. The results complied with statistical criteria set forth by the SPF-test method EN ISO 24444:2010.

The results are summarized in table 7 below. The results show that the inventive product has a very high SPF of 50 (example 12). Strong protection is still provided 8 hours after application to the skin (example 13). The UV protection properties are significantly better than for the benchmark product (comparative examples 14, 15).

TABLE 7

Results of examples 12 to 15. Examples 14 and 15 are comparative

| Ex. | composition | application time before measuring | labelled SPF | labelled protection category | 95% confidence interval | SPF mean | standard deviation |
|---|---|---|---|---|---|---|---|
| 12 | example 8 | 30 min | 50 | high | 49.3-54.3 | 51.8 | 3.5 |
| 13 | example 8 | 8 h | 30 | high | 28.2-32.6 | 30.4 | 3.0 |
| 14 | Kelo-Cote UV | 30 min | 39 | high | 29.1-32.4 | 30.7 | 2.3 |
| 15 | Kelo-Cote UV | 8 h | 20 | medium | 18.5-23-2 | 20.8 | 3.3 |

Examples 16 and 17—Protection Against UVA and Critical Wavelength

The UVA-protection was assessed according to ISO 24443:2012 "Determination of sunscreen UVA photoprotection in vitro". The standard is for determining UVA-protection provided by sun-screen products. The method determines in-vitro UVA-protection factor (UVAPF) in correlation to the labeled UVB-protection factor. The test is based on is measuring UV-transmittance through a thin film of the sunscreen sample spread on a roughened substrate, before and after exposure to a controlled dose of UV-radiation from a defined UV-source. For irradiation, a dose of UV-light is chosen specified for the product on test.

The critical wavelength $\lambda_c$ was determined according to the "Critical wavelength" values of sunscreen products"

published by the COLIPA "in-vitro UV Protection Method Task Force" of (March 2011). The critical wavelength $\lambda_c$ value for the test product is defined as that wavelength up to which the area under the absorbance spectrum for the irradiated product from 290 nm is 90% of the integral of the absorbance spectrum from 290 nm to 400 nm. The test is based on measuring UV-transmittance through a thin film of sunscreen sample spread on a roughened substrate, before and after exposure to a controlled dose of UV-radiation from a defined UV-source. For irradiation a dose of UV-light is chosen specified for the product on-test. The critical wavelength is considered to be a measure of the breadth of sunscreen protection. Filters are then classified as 'broad spectrum', having a significant part of their absorbance in the UVA, when the critical wavelength is longer than 370 nm.

The results are summarized in table 8 below. The results show that the UVA protection of the inventive product in example 16 is about 45.5%, whereas UVA protection of the comparative product is only 4.2%. According to industry standards, only the inventive composition may be labelled as UVA protective. Further, the critical wavelength of the inventive composition is significantly higher which indicates that the composition provides broad spectrum protection.

TABLE 8

Results of example 16 and comparative example 17

| Ex. | composition | labelled SPF in vivo | UVA dose used [J/cm²] | UVAPF | UVAPF/ SPF | number of plates | critical wavelength $\lambda_c$ [nm] |
|---|---|---|---|---|---|---|---|
| 16 | example 8 | 50 | 28.0 | 22.73 | 0.455 | 4 | 377 |
| 17 | Kelo-Cote UV | 30 | 1.58 | 1.26 | 0.042 | 4 | 330 |

Example 18—Scar Healing

A double blind, placebo controlled, randomized clinical study was carried for assessment of efficacy of the inventive composition in the treatment of hypertrophic, keloid or cosmetically unsatisfactory scars. The trial was carried out with a POSAS questionnaire.

The Patient and Observer Scar Assessment Scale (POSAS) is a questionnaire to assess scar quality. The POSAS is widely used and accepted in the technical field and has been used for a large number of clinical trials. It consists of two separate six-itemed scales, observer and patient scale which based on the 10-point system. The observer scale has vascularity, pigmentation, thickness, relief, pliability, and surface area criterions. The observer scale of the POSAS consists of six items (vascularity, pigmentation, thickness, relief, pliability and surface area). All items are scored on a scale ranging from 1 (like normal skin') to 10 ('worst scar imaginable'). The sum of the six items results in a total score of the POSAS observer scale. Categories boxes are added for each item. Furthermore, an overall opinion is scored on a scale ranging from 1 to 10. All parameters should preferably be compared to normal skin on a comparable anatomic location. The patient scale comprises six standard questions to be answered by the patient. The answers are given on a scale from 1 to 10. Further information regarding the questionnaire can be found at www.posas.org.

POSAS was carried out in a placebo controlled double blind study with intra-individual control with patients having chirurgical scars. The study was carried out with 8 patients having scars of a length of at least 2 cm. Two comparable scars each were treated with an inventive composition of example 8 above. For comparison, patients were treated with the commercially available scar gel KELO-COTE UV from Sinclair, DE, which is the market leader and benchmark product. Overall, 5 patients were treated with the inventive product and 3 patients with the comparative product, the discrepancy being due to random selection of the probe in the trial. The individuals applied the gel twice a day over a time span of three months. The scars were evaluated according to the POSAS scale by the doctor and patient 1 day before first application, after 6 weeks and after 3 months. The trial was carried out according to the principles of the declaration of Helsinki (World medical association 2000) and the rules of "Good Clinical Practice" (ICH 1998). The results are summarized in table 9 (observer scale) and 10 (patient scale).

TABLE 9

POSAS observer scale, criteria and results after 3 months. Possible results range from 1 = "normal skin to 10" = "worst imaginable scar"

| parameter | explanation | coating inventive | Kelo-Cote UV |
|---|---|---|---|
| vascularity | Presence of vessels in scar tissue assessed by the amount of redness, tested by the amount of blood return after blanching with a piece of Plexiglas | 1.4 | 5.3 |
| pigmentation | Brownish coloration of the scar by pigment (melanin); apply Plexiglas to the skin with moderate pressure to eliminate the effect of vascularity | 1.6 | 5.3 |
| thickness | Average distance between the subcutical-dermal border and the epidermal surface of the scar | 2.0 | 6.0 |
| relief | The extent to which surface irregularities are present (preferably compared with adjacent normal skin) | 2.0 | 6.0 |
| pliability | Suppleness of the scar tested by wrinkling the scar between the thumb and index finger | 1.4 | 6.3 |
| surface area | Surface area of the scar in relation to the original wound area | 2.0 | 5.7 |
| Overall opinion | | 1.6 | 6.0 |

The results provide evidence of a significant effect of the inventive product on scar healing. For all patients treated with the inventive product, after 3 months the scars were healed completely or almost completely and the respective skin portion was identical or highly similar to normal skin. Notably, most patients already reported significant improvements after a few weeks (data not shown). In contrast, all patients treated with the benchmark product for 3 months still had pronounced scars.

TABLE 10

POSAS patient scale, questions and results after 3 months

| Question | coating inventive | Kelo-Cote UV |
|---|---|---|
| possible answers ranging from 1 = "no, not at all" to 10 = "yes, very much" | | |
| has the scar been painful the past few weeks? | 1.2 | 3.0 |
| has the scar been itching the past few weeks? | 1.0 | 4.7 |
| possible answers ranging from 1 = "no, as normal skin" to 10 = "yes, very different" | | |
| is the scar color different from the color of your normal skin at present? | 2.0 | 6.7 |
| is the stiffness of the scar different from your normal skin at present? | 2.0 | 7.3 |
| is the thickness of the scar different from your normal skin at present? | 1.8 | 7.3 |
| is the scar more irregular than your normal skin at present? | 2.0 | 7.3 |
| possible answers ranging from 1 = "as normal skin" to 10 = "very different" | | |
| what is your overall opinion of the scar compared to normal skin? | 1.6 | 7.0 |

The patients results demonstrate confirm the significant effect of the inventive coating on scar healing. In contrast, all patients treated with the benchmark product reported pronounced scars after 3 months.

Example 19: Ease of Application and Mechanical Stability of Coating

Together with the POSAS questionnaire described above in example 18, additional questions were asked to the patients relating to application and stability of the dried products on the scars. Thus, the supplementary questionnaire was part of the double blind, placebo controlled, randomized clinical study. The questions and results are summarized in the following.
A) How fast did the gel dry?
All patients treated with the inventive composition reported drying within 10 to 40 seconds. In contrast, all patients treated with the benchmark product reported that drying requires more than 30 minutes.
B) Is the gel film undamaged despite movement or dressing?
All patients treated with the inventive composition answered "yes". In contrast, the patients treated with the benchmark product answered "no".
C) How is stability of the gel film upon contact with water/moisture?
The patients treated with the inventive composition answered that the stability is "very good" (4 patients) or "good" (1 patient). In contrast, all patients treated with the benchmark product answered that the stability is "unsufficient".
D) For how long does the gel film remain on the skin?
All patients treated with the inventive composition reported that the film remained on the skin for at least 6 hours or at least 8 hours. In contrast, all patients treated with the benchmark product reported that the film remained on the skin for less than 60 minutes.
E) Is the gel film applied in the morning still present at the application time in the evening?
All patients treated with the inventive composition reported that 100% or about 50% or the film was still present. In contrast, all patients treated with the benchmark product reported that the film was not present any more or that about 30% was still present.

Overall, the results demonstrate that the inventive composition is applied much more conveniently and far more stable on the skin. From the data it can be deduced that only the inventive coating is suited for convenient regular use and normal activities. It provides long-term protection for up to 8 hours and does not compromise typical activities of the user such as dressing, standard outdoor activities or contact with moisture by rain, washing or sweating. Moreover, the inventive coating can be applied again conveniently in because of the rapid drying time of less than 1 minute. In contrast, the benchmark product has a low stability and frequent application is unpractical because of the time required for drying.

In contrast, the benchmark product has a very limited stability and becomes ineffective upon contact with moisture or moderate mechanical stress. Frequent application is unpractical in view of the long drying time.

The invention claimed is:

1. A composition comprising
   (a) at least one film-forming polymer, which does not comprise silicon,
   (b) at least one organic UV filter, and
   (c) at least one organic solvent,
   wherein the composition is a liquid solution at 20° C. with no solids dispersed therein, wherein components (a) and (b) are dissolved in solvent (c),
   wherein the ratio of the total amounts in weight percent of organic UV filters (b) to film-forming polymers (a) is below 6.5,
   wherein the overall amount of UV filters (b) in the composition is at least 10% (w/w),
   wherein the composition comprises at least 5% (w/w) of film-forming polymers (a),
   wherein the composition forms a solid coating after topical application to skin,
   wherein the composition does not comprise other polymers than the film-forming polymers (a), and
   wherein the composition does not comprise a silicone.

2. The composition of claim 1, wherein the film-forming polymer (a) is an amphiphilic copolymer.

3. The composition of claim 1, wherein the film-forming polymer (a) is an acrylate/amide copolymer with alkyl groups having 6 to 16 carbon atoms.

4. The composition of claim 1,
   wherein the composition comprises less than 5% (w/w) water, and/or
   wherein the ratio of the total amounts in weight percent of organic UV filters (b) to film-forming polymers (a) is above 1 to below 6.5.

5. The composition of claim 1, wherein the solvent (c) is an aliphatic alcohol, and/or
   wherein the composition comprises at least one additive (d).

6. The composition of claim 1, consisting of
   (a) between 5 and 50% (w/w) film-forming polymers, which do not comprise silicon,
   (b) between 10 and 60% (w/w) organic UV filters,
   (c) between 30 and 90% (w/w) organic solvents,
   (d) between 0 to 25% (w/w) additives,
   and less than 5% (w/w) water.

7. The composition of claim 1, wherein the composition forms a solid coating after topical application to a scar.

8. The composition of claim 1, wherein the composition has a sun protection factor (SPF) of at least 10.

9. A method for covering a scar, the method comprising
(A) providing a composition of claim 1,
(B) applying the composition locally and topically to a scar of an individual, and
(C) optionally drying the composition.

10. A method for preparing a composition of claim 1, comprising the steps of
(i) dissolving the film-forming polymers (a) in the organic solvent (c) to obtain phase A,
(ii) providing the UV filters (c) in liquid form, optionally at enhanced temperature, as a phase B, and
(iii) mixing phase A and phase B.

11. A device for topical application of a composition of claim 1 to the skin of an individual, wherein the device comprises a composition of claim 1.

12. The method of claim 9, wherein the method is non-therapeutic.

13. The method of claim 9, wherein the method supports healing of the scar.

14. The composition of claim 2, wherein the copolymer comprises carboxyl groups and alkyl groups and wherein the carboxyl groups are attached to the polymer main chain and the alkyl groups are side chains.

15. The composition of claim 3, wherein the acrylate/amide copolymer is an acrylate/octylacrylamide copolymer.

16. The composition of claim 5, wherein the solvent (c) is methanol, ethanol, propanol or isopropanol, and/or
wherein the composition comprises at least one additive (d), which is selected from moisturizers, photoprotective agents, oils, fats, waxes, glycerides, surfactants, thickening agents, fragrances, dyes, preservatives, photostabiliziers, antioxidants, skin care agents and pharmaceutical agents.

17. The composition of claim 7, wherein the composition forms a solid coating after topical application to a scar within less than 1 minute.

18. The composition of claim 8, wherein the composition has a sun protection factor (SPF) of at least 40.

19. The method of claim 10, wherein mixing phase A and phase B comprises adding phase B to phase A.

20. The device of claim 11, wherein the device is in the form of a roller.

21. The composition of claim 1, which comprises between 0 to 10% (w/w) additives.

22. A composition consisting of
(a) between 5 and 50% (w/w) film-forming polymers, which do not comprise silicon,
(b) between 10 and 60% (w/w) organic UV filters,
(c) between 30 and 90% (w/w) organic solvents,
(d) between 0 to 25% (w/w) of at least one additive,
and less than 5% (w/w) water,
wherein the composition is a liquid solution at 20° C. with no solids dispersed therein, wherein components (a) and (b) are dissolved in solvent (c),
wherein the ratio of the total amounts in weight percent of organic UV filters (b) to film-forming polymers (a) is below 6.5,
wherein the composition forms a solid coating after topical application to skin,
wherein the at least one additive is selected from photoprotective agents, hydrophobic compounds selected from fats and waxes; surfactants, thickening agents, fragrances, dyes, preservatives, photostabilizers, antioxidants and pharmaceutical compounds, and
wherein the composition does not comprise a silicone.

23. The composition of claim 22, wherein the film-forming polymer (a) is an amphiphilic copolymer.

24. The composition of claim 22, wherein the film-forming polymer (a) is an acrylate/amide copolymer with alkyl groups having 6 to 16 carbon atoms.

25. The composition of claim 22, wherein the ratio of the total amounts in weight percent of organic UV filters (b) to film-forming polymers (a) is above 1 to below 6.5.

26. The composition of claim 22, wherein the solvent (c) is an aliphatic alcohol, and/or
wherein the composition comprises at least one additive (d).

27. The composition of claim 22, wherein the composition forms a solid coating after topical application to a scar.

28. The composition of claim 22, wherein the composition has a sun protection factor (SPF) of at least 10.

* * * * *